US00PP11496P

United States Patent [19]

Layne

[11] Patent Number: Plant 11,496

[45] Date of Patent: Aug. 29, 2000

[54] 'AC HARFLAME' NECTARINE

[75] Inventor: Richard E. C. Layne, Ontario, Canada

[73] Assignee: Agriculture and Agri-Food Canada, Ontario, Canada

[21] Appl. No.: 09/025,756

[22] Filed: Feb. 18, 1998

[51] Int. Cl.[7] ..... A01H 5/00

[52] U.S. Cl. ..... Plt./192

[58] Field of Search ..... Plt./192, 190

[56] References Cited

U.S. PATENT DOCUMENTS

P.P. 4,791 11/1981 Anderson ..... Plt./192
P.P. 10,022 9/1997 Zaiger et al. ..... Plt./190

OTHER PUBLICATIONS

Sharon Hill, "Scientist Peachy Keen on New Fruit Varieties", Windsor Star, p. B1, Feb. 5, 1996.

*Primary Examiner*—Howard J. Locker
*Assistant Examiner*—Wendy Baker
*Attorney, Agent, or Firm*—Flynn, Thiel, Boutell & Tanis, P.C.

[57] ABSTRACT

A new and distinct variety of nectarine tree which has been given the designation 'AC Harflame', that is cold hardy, disease resistant, productive and bears an attractively colored fruit of good size and quality that is suitable for long distance shipping.

2 Drawing Sheets

FIELD OF THE INVENTION

The present invention relates to a nectarine variety and more specifically to a nectarine variety that is a cold hardy, disease resistant, attractively colored nectarine of medium size and good quality suitable for the fresh market.

BACKGROUND OF THE INVENTION

'AC Harflame' is a fresh market nectarine which is distinguished in characteristics from the varieties similar to it, 'Fantasia', 'Harblaze', 'Hardired' and 'Harko'. 'Harblaze' is the variety it most closely resembles. 'AC Harflame' has been described by Richard E. C. Layne, HortScience, vol. 31 (6): 1050–1051, October, 1996.

'AC Harflame' nectarine (*Prunus persica* (L.) Batsch) was released for the Ontario fresh market in 1996 following application for Plant Breeders Rights in Canada on Oct. 11, 1995 (Application No. 95-647). It is an early season nectarine that ripens seven days before Redhaven peach. This variety was recommended for commercial introduction in Canada by members of the Western Ontario Fruit Testing Association (WOFTA) on the basis of generally favorable performance in regional trials in southern Ontario coordinated by WOFTA. 'AC Harflame' should be adapted to northern regions where Redhaven peach is successfully grown. To Applicant's knowledge, none of the prior art varieties referred to herein are patented.

SUMMARY OF THE INVENTION

The fruit of 'AC Harflame' matures earlier than the fruit of 'Harko', 'Hardired' and 'Fantasia'. It has no anthocyanin in the fruit flesh while the reference varieties have anthocyanin present. Trees of 'AC Harflame' have a more erect growth habit than the reference varieties.

DETAILED DESCRIPTION OF THE INVENTION

Figure 1:
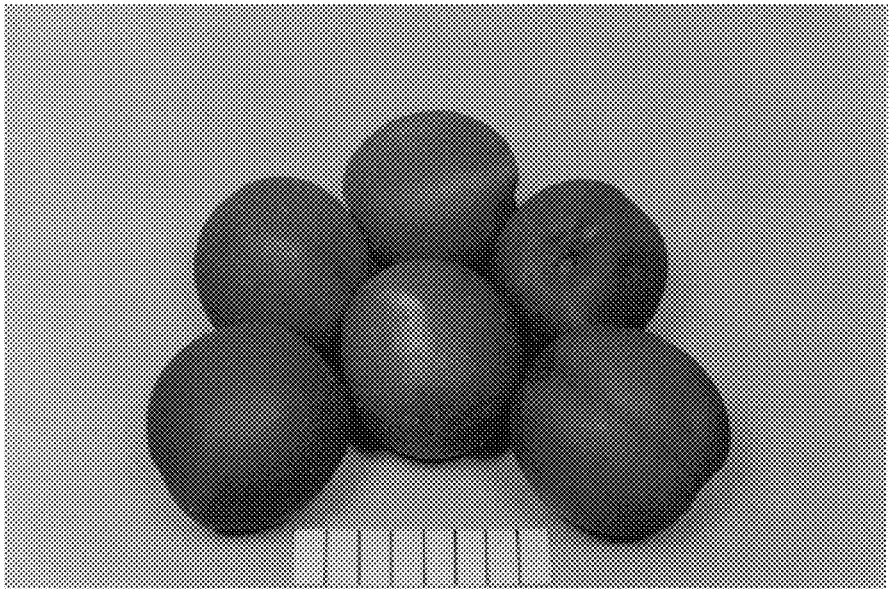
FIG. 1 is a photographic illustration of the whole fruit of 'AC Harflame' nectarine.
Figure 2:
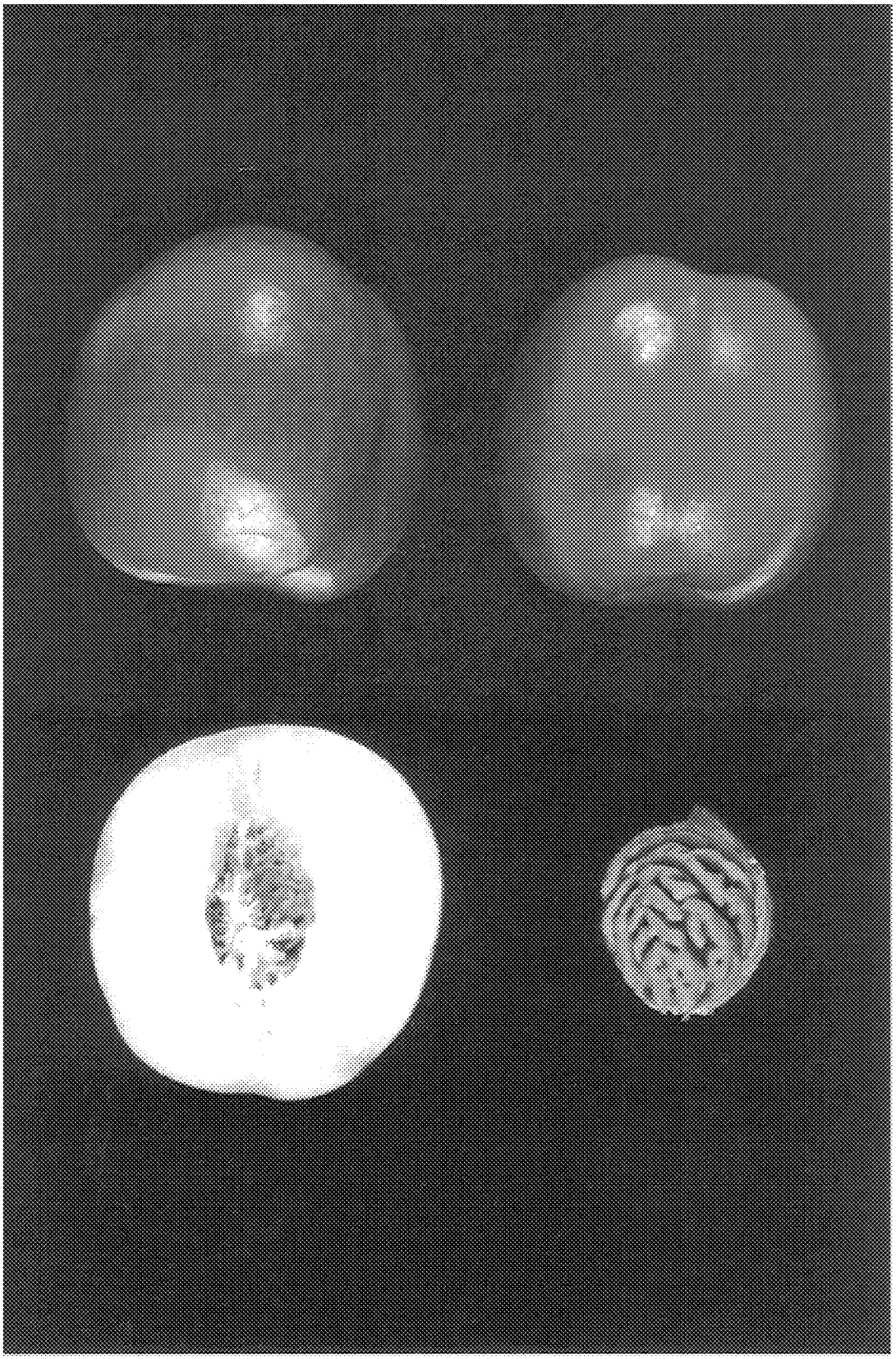
FIG. 2 is a photographic illustration of two whole fruits, bisected fruit and stone. The color of the skin, flesh, stone and stone cavity are illustrated.

'AC Harflame' resulted from a controlled cross of 'Fantasia'×H7343017, made at the Agriculture and Agri-Food Canada research station in Harrow, Ontario. 'Fantasia' originated from the cross 'Gold King'×'Red King' (open pollinated) and H7343017 originated from the cross 'Stark Delicious'×'Hardired'. 'AC Harflame' was selected as a seedling hybrid. It was then propagated by budding on peach seedling rootstocks. It was tested under the experimental designation HW107 in regional trials coordinated by the Western Ontario Fruit Testing Association. 'AC Harflame' remains stable through succeeding asexual propagation and it is self-pollinated. The color terminology is in accordance with The Royal Horticultural Society Colour Chart.

'AC Harflame' is a non-spur type variety with strong vigor. The tree habit of 'AC Harflame' is more erect than the reference varieties and the tree bark is reddish-brown in color in mid-summer and reddish-brown with a silvery sheen in winter. The leaves are medium to large in size for 'AC Harflame' compared with the small size of 'Hardired' and small to medium size of 'Fantasia'. The leaf blade is up-folded in profile and the tip is recurved downwards. The angle at the base and tip of the leaf blade is acute. The leaf blade of 'AC Harflame' has anthocyanin present while 'Harko', 'Hardired' and 'Fantasia' have no anthocyanin. The leaf margins are serrated. The leaf petiole is medium in length for 'AC Harflame' while 'Harko', 'Hardired' and 'Fantasia' have slightly shorter petioles. The petiole has nectaries which are kidney-shaped. 'AC Harflame' normally has more than two nectaries while 'Harko' and 'Hardired' have two. No stipules are observed in mid-summer.

The flowering shoot of 'AC Harflame' has weak anthocyanin coloration while 'Hardired' and 'Fantasia' have medium to strong anthocyanin. The density of flower buds is high for 'AC Harflame' while the density is medium to high for 'Fantasia'. The time of beginning of flowering is mid-season for 'AC Harflame' while it is slightly later for 'Hardired'. Flower shape is rosaceous and the calyx is reddish-brown in color. The petals are rounded in shape and large in size. The petals are medium pink in color for 'AC Harflame' while they are light pink for 'Hardired'. Petal striping is absent and there are five petals per flower. The stamens of 'AC Harflame' are shorter in length when compared to the petals and there is one pistil. The stigma is positioned above the anthers for 'AC Harflame' while it is at the same level for 'Harko' and 'Hardired'. The anthers have pollen present and the ovary has no pubescence. The duration of flowering is medium for 'AC Harflame', long for 'Harko' and medium to long for 'Hardired'.

The fruit matures early to mid-season for 'AC Harflame', mid-season for 'Harko', mid to late season for 'Hardired' and late for 'Fantasia'. The picking season is short for 'AC Harflame' and long for 'Harko'. The tendency to natural falling of fruit is absent to very weak for 'AC Harflame' and weak for 'Harko', 'Hardired' and 'Fantasia'. Fruit size is medium to large for 'AC Harflame', large for 'Harblaze', medium for 'Harko' and small to medium for 'Hardired'. The shape of the fruit in profile view is rounded compared with the oblong shape of 'Hardired'. The shape of the fruit tip is dimpled. Symmetry along the suture is symmetric for 'AC Harflame' while 'Fantasia' is asymmetric. The prominence of the suture is low for 'AC Harflame' while it is low to medium for 'Harblaze' and medium for 'Fantasia'. The depth of the stem cavity is medium for 'AC Harflame' while it is medium to deep for 'Fantasia'. The width of the stem cavity is narrow for 'AC Harflame' compared with the medium width of 'Harko' and 'Hardired' and medium to broad width of 'Fantasia'. The ground color of the skin is yellow for 'AC Harflame' while it is greenish yellow for 'Harko' and 'Hardired'. Anthocyanin coloration of the skin is bright red while 'Harko', 'Hardired' and 'Fantasia' have dark red anthocyanin. The proportion of fruit skin with anthocyanin coloration is heavy for 'AC Harflame' while it is very heavy for 'Harko' and 'Hardired'. The anthocyanin is uniformly distributed over the skin and there is no pubescence on the skin. The skin is medium in thickness while 'Fantasia' has thin to medium skin. Adherence of the skin to the flesh is weak for 'AC Harflame' while it is strong for 'Fantasia'. The fruit flesh is medium to firm for 'AC Harflame' while the flesh is slightly firmer for 'Fantasia' and less firm for 'Harko' and 'Hardired'. The ground color of the flesh is yellow to orange-yellow and there is no anthocyanin coloration directly under the skin of 'AC Harflame' while 'Harko' and 'Hardired' have anthocyanin under the skin. The fruit of 'AC Harflame' has no anthocyanin present in the flesh and around the stone while the reference varieties have anthocyanin in the flesh and 'Hardired' and 'Fantasia' have anthocyanin around the stone. The flesh of 'AC Harflame' is not stringy while the flesh of 'Harko' is somewhat stringy. The texture of the flesh is melting and the acidity is intermediate. The flesh of 'AC Harflame' is juicy while 'Fantasia' has less juiciness.

The stone of 'AC Harflame' is medium to large in size and elongate in shape. The percentage of split or shattered stones is low for 'AC Harflame' while it is slightly lower for the reference varieties. 'AC Harflame' has no adherence of the stone to the flesh while 'Harko' has slight adherence. The length of the stone is 29.8 mm, the width 23.3 mm and the thickness 16.2 mm.

'AC Harflame' differs from 'Harblaze', the variety it most closely resembles in the following ways: trees of 'AC Harflame' are more erect in growth habit than 'Harblaze', flower bud density is greater than 'Harblaze' and generally in groups of two or more. Petals of 'AC Harflame' are darker pink than 'Harblaze' and fruit size is smaller than 'Harblaze'. The suture of 'AC Harflame' is less prominent than for 'Harblaze' and the skin is thinner than 'Harblaze'. Adherence of the skin to the flesh is much weaker for 'AC Harflame' than for 'Harblaze'. The flesh of 'AC Harflame' is not as firm as 'Harblaze' and there is no anthocyanin coloration of the flesh compared with 'Harblaze' where it is present. The percentage of shattered stones is slightly greater for 'AC Harflame' than for 'Harblaze'. 'AC Harflame' is slightly more cold hardy than 'Harblaze' in natural and controlled freezing tests. Both varieties ripen in the early to mid-season but 'AC Harflame' typically ripens three days before 'Harblaze'. 'AC Harflame' will hold for 2 to 3 weeks in common cold storage when picked shortly before ripening.

Additional characteristics of 'AC Harflame' nectarine and the reference varieties are shown in Chart 1 below.

CHART 1

Plant vigor: Average growth (length) of 1 year old shoots
- *Harflame.*—418 mm.
- *Harblaze.*—331 mm.
- *Harko.*—403 mm.
- *Hardired.*—372 mm.
- *Fantasia.*—364 mm.

Colors:
- *Fruit skin (ground color).—Light yellow/slight green,* 5A.
- *Fruit skin (blush).*—45A.
- *Flesh.*—12B.
- *Pit cavity.—Dark yellow* 16A.
- *Pit.*—164A.
- *Leaf (dorsal).*—141B.
- *Leaf (ventral).*—138A.

Trunk size/texture: Average trunk size (circumference) of 4 year old trees:
- *Harflame.*—194 mm.
- *Harblaze.*—174 mm.
- *Harko.*—181 mm.
- *Hardired.*—178 mm.
- *Fantasia.*—203 mm.

The trunks of all the trees are painted with white latex paint to protect them from sun damage and therefore is very difficult to determine colour and texture of the bark on the trunk.

Crotch Angles: Branch size and crotch angles are controlled by training and pruning methods of the trees. The natural growth habit of the tree is therefore not seen since poorly angled (narrow) branches are pruned out. Remaining branches are approximately 70 degrees from vertical position of the central leader of the tree.

Lenticels: Relative number and size.
- *Harflame.*—Few and small (1 mm in size).
- *Harblaze.*—Few and small.
- *Harko.*—Few and small.
- *Hardired.*—Very few and very small (smaller than 1 mm).
- *Fantasia.*—Few and small.

Avg. bloom date/duration:
- *Harflame.*—May 4, 4 days.
- *Harblaze.—May* 4, 4 days.
- *Harko.*—May 3, 4 days.
- *Hardired.*—May 5, 4 days.
- *Fantasia.*—May 3, 4 days.

Avg. ripe dates/duration:
- *Harflame.*—August 6, 4 days.
- *Harblaze.*—August 9, 4 days.
- *Harko.*—August 12, 4 days.
- *Hardired.*—August 16, 4 days.

*Fantasia.*—September 3, 4 days.

Fruit characteristics:

*Harflame.*—Height (mm)=63.7, Width (mm)=62.4, Weight (g)=142.0.

*Harblaze.*—Height (mm)=67.6, Width (mm)=64.9, Weight (g)=162.0.

*Harko.*—Height (mm)=57.2, Width (mm)=61.4, Weight (g)=124.8.

*Hardired.*—Height (mm)=56.6, Width (mm)=57.2, Weight (g)=104.7.

*Fantasia.*—Height (mm)=68.5, Width (mm)=64.1, Weight (g)=153.3.

Sugar content (Brix):

*Harflame.*—11.3.

*Harblaze.*—9.3.

*Harko.*—9.6.

*Hardired.*—7.8.

*Fantasia.*—10.9.

Productivity: This is evaluated on a rating system from 1 to 10 where 1 is very little or no crop, 5 is a commercially acceptable amount of fruit on a tree, and 10 represents a crop load so heavy it would break the tree if left un-thinned. All the varieties mentioned for the descriptor having average ratings of 5.

Nectaries:

*Harflame.*—kidney-shaped.

*Harblaze.*—kidney-shaped.

*Harko.*—kidney-shaped.

*Hardired.*—kidney-shaped.

*Fantasia.*—kidney-shaped.

Petioles:

*Harflame.*—Length (mm)=9.7, width (mm)=1.3.

*Harblaze.*—Length (mm)=9.7, width (mm)=1.3.

*Harko.*—Length (mm)=8.1, width (mm)=1.3.

*Hardired.*—Length (mm)=7.1, width (mm)=1.2.

*Fantasia.*—Length (mm)=10.3, width (mm)=1.4.

PERFORMANCE

'AC Harflame' was tested along with the reference varieties at the Ridge Farm, Harrow Research Centre, Harrow, Ontario, from 1990 to 1995 is a completely random design with three replications. Trees were spaced 3 meters apart in the row and rows were spaced 5.5 meters apart. Trees were trained to a modified central leader and standard orchard management practices were followed according to OMAFRA Publ. 360 Fruit Production Recommendations. Comparative performance was assessed on bearing trees and provided the data for the objective description form. Results are shown in Table 1.

TABLE 1

Comparison table for 'AC Harflame'

| CHARACTERISTICS | 'AC HARFLAME' | 'HARBLAZE'* | 'HARKO'* | 'HARDIRED'* | 'FANTASIA'* |
|---|---|---|---|---|---|
| Length of leaf blade (mm) | | | | | |
| mean | 142.8 | 142.9 | 140.2 | 117.4 | 131.9 |
| range | 104–175 | 118–172 | 111–169 | 88–138 | 109–164 |
| standard deviation | 15.0 | 15.4 | 14.7 | 11.7 | 13.6 |
| number measured | 30 | 30 | 30 | 30 | 30 |
| Width of leaf blade (mm) | | | | | |
| mean | 35.2 | 32.6 | 32.3 | 30.2 | 33.6 |
| range | 27–40 | 27–38 | 25–40 | 22–37 | 27–43 |
| standard deviation | 2.9 | 2.7 | 3.6 | 3.5 | 3.4 |
| number measured | 30 | 30 | 30 | 30 | 30 |
| Duration of flowering | medium | medium | long | medium to long | medium |
| Time of maturity | early to medium | early to medium | medium | medium to late | late |
| Ground color of fruit skin | yellow | yellow | greenish-yellow | greenish-yellow | yellow |
| Proportion of fruit surface with anthocyanin coloration on the skin | heavy (±75%) | heavy (±75%) | very heavy (>75%) | very heavy (>75%) | heavy (±75%) |
| Prominence of fruit suture | low | low to medium | low | low | medium |
| Adherence of fruit skin to flesh | weak | strong | weak | weak | strong |
| Anthocyanin coloration of the flesh | absent | present | present | present | present |

*reference varieties

I claim:

1. A new and distinct nectarine tree variety substantially as shown and described herein.

* * * * *